United States Patent [19]

Aunet et al.

[11] Patent Number: 4,933,092
[45] Date of Patent: Jun. 12, 1990

[54] METHODS AND DEVICES FOR THE SEPARATION OF PLASMA OR SERUM FROM WHOLE BLOOD

[75] Inventors: Diane L. Aunet, Waukegan; Gradimir G. Gerogevich, Mundelein; Tzyy-Wen Jeng, Vernon Hills; Gary M. Oosta, Gurnee; Neal A. Siegel, Deerfield, all of Ill.

[73] Assignee: Abbott Laboratories, Abbott Park, Ill.

[21] Appl. No.: 335,064

[22] Filed: Apr. 7, 1989

[51] Int. Cl.$^5$ .................. B01D 37/00; B01D 39/14
[52] U.S. Cl. .................. 210/729; 210/295; 210/314; 210/335; 210/510.1; 210/730; 210/732; 210/806; 422/101; 435/2; 436/177
[58] Field of Search .............. 210/206, 259, 295, 314, 210/373.1, 335, 510.1, 651, 702, 729, 730, 732, 806; 435/2; 422/101; 436/177, 178, 808

[56] References Cited

U.S. PATENT DOCUMENTS

| | | | |
|---|---|---|---|
| 3,888,629 | 6/1975 | Bagghawe | 436/804 |
| 3,902,964 | 9/1975 | Greenspan | 435/2 |
| 4,464,254 | 8/1984 | Dojki et al. | 210/136 |
| 4,477,575 | 10/1984 | Vogel et al. | 436/177 |
| 4,594,327 | 6/1986 | Zuk | 436/514 |
| 4,753,776 | 6/1988 | Hillman et al. | 422/101 |
| 4,820,644 | 4/1989 | Schäfer et al. | 422/101 |

FOREIGN PATENT DOCUMENTS

| | | |
|---|---|---|
| 133895 | 3/1985 | European Pat. Off. . |
| 203459 | 3/1986 | European Pat. Off. . |
| 2186205 | 8/1987 | United Kingdom . |

Primary Examiner—W. Gary Jones
Attorney, Agent, or Firm—Priscilla E. Porembski; Daniel W. Collins; Thomas D. Brainard

[57] ABSTRACT

A device and method for permitting the separation of plasma or serum from whole blood. The device comprises a matrix of hydrophilic sintered porous material to which at least one red blood cell agglutinating agent has been applied. According to a first method of using the device, a sample of whole blood is applied to a first end of the matrix and the red blood cells within the sample come in contact with the agglutinating agents present in the matrix. The blood cells agglutinate, and are entrapped in the interstices of the matrix, while substantially blood-cell-free serum or plasma accumulates near the outlet of the device. A filter means in liquid receiving relationship with the matrix functions to wick the serum or plasma from the matrix.

According to an alternative aspect of the invention, a filter means in liquid receiving relationship with the outlet of the matrix functions to retain any blood cells which pass through the matrix is the filter means wicks the plasma or serum from the matrix. Additional agglutinating agents may be incorporated within the filter means to facilitate retention of blood cells which pass through the matrix.

20 Claims, 2 Drawing Sheets

METHODS AND DEVICES FOR THE SEPARATION OF PLASMA OR SERUM FROM WHOLE BLOOD

BACKGROUND OF THE INVENTION

1. Field of the Invention

The present invention relates generally to methods for separating plasma or serum from whole blood. More particularly, the invention relates to devices capable of separating plasma or serum from whole blood comprising a hydrophilic sintered porous material in which at least one red blood cell agglutinating agent has been incorporated. Agglutinated blood cells are removed from whole blood by the sieving action of the matrix of the sintered porous material, and optional additional filter means.

2. Background

Modern clinical diagnostic methods are routinely carried out on blood samples. Unfortunately, red blood cells present in whole blood scatter and absorb light thus interfering with assay methodologies which measure either reflected or transmitted light. Other cells may interfere with particular determinations; for example, cholesterol determinations can be effected by cholesterol present in cell membranes. For this reason, many assay methodologies are carried out on plasma or serum which must be separated from a whole blood sample.

Centrifugation is a well known method in the art by which plasma (before clotting) and serum (after clotting) is separated from whole blood. Stratifying whole blood by centrifugation, however, is time consuming and requires cumbersome laboratory equipment. The use of red blood cell agglutinating agents such as those disclosed in Van Oss, et al., *Vox. Sang.*, vol. 34, pp 351–361 (1978) can be helpful in carrying out centrifugation and other red blood cell separation techniques.

Dojki, et al., U.S. Pat. No. 4,464,254, issued Aug. 7, 1984, disclose a piston device capable of isolating serum from an already stratified blood sample. The device consists of a piston head connected to an open-ended sampling tube. The piston head is composed of a one way valve under which is located a cavity containing a porous plastic filter body. Insertion of the piston head-sampling tube assembly into a test tube containing a stratified sample of blood allows serum to pass through the filter body and valve into the interior of the sampling tube. The volume and purity of the serum which can be separated from the whole blood is contingent upon the completeness of the stratification of the blood.

Vogel, et al., U.S. Pat. No. 4,477,575, issued Oct. 16, 1984, disclose a device and a process using the device to separate serum from whole blood by causing whole blood to pass into and through a layer of glass fibers with diameters from 0.2 to 5 microns and with a density of 0.1 to 0.5 g/cm$^3$. The volume of plasma or serum which can be separated from whole blood by this device is disclosed to be less than 50% of the absorption volume of the glass fiber layer.

Zuk, U.S. Pat. No. 4,594,327, issued June 10, 1986, discloses an analytical method wherein a whole blood sample is combined with a red blood cell binding agent and the mixture is then filtered through a solid bibulous element to which is bound at least one specific binding pair member so as to remove the agglutinated red blood cells. The patent discloses anti-red blood cell antibodies, polymeric amino acids, such as polylysine, and lectins, such as wheat germ agglutinin, as suitable red blood cell binding agents for causing the aggregation of red blood cells in whole blood.

Hillman, et al., U.S. Pat. No. 4,753,776, issued June 28, 1988, disclose a device and a process using the device to separate serum from whole blood using capillary action to pass whole blood through a glass microfiber filter. The patent discloses an alternative embodiment in which whole blood is passed through a filter to which red blood cell agglutinins have been attached. Rather than retaining the red blood cells, however, the filter disclosed merely retards their flow, eventually allowing their escape.

Trasch, et al., EPO Publication No. 133,895, published Mar. 13, 1985, disclose a red blood cell retaining substrate and a process using the substrate for retaining red blood cells on filters thus allowing the recovery of plasma from whole blood. The red blood cell-retaining substrates of the invention are stated to induce coagulation, but not hemolysis, so that the coagulated corpuscular components can be removed on a filter, while the plasma passes through. The publication discloses alternative embodiments where the retaining substrate is incorporated into the filter or into a pre-filter layer. The publication states that absorptive, porous, liquid-permeable carriers or filters, in the form of paper, fleece, gel or tissues, comprised of cellulose, wool, glass fiber, asbestos, synthetic fibers, polymers or mixtures of the same, can be used as the absorptive materials for the retaining zone.

Most portable techniques for the separation of serum or plasma are limited with respect to speed and serum yield efficiency. Blood separation devices utilizing glass fiber membranes, for example, tend to separate serum at a relatively slow speed and tend to retain significant quantities of serum or plasma in the interstices of the membrane. Accordingly, there exists a desire in the art for improved devices providing rapid and efficient methods for serum and plasma separation.

SUMMARY OF THE INVENTION

The present invention relates to improved methods, devices and kits for separating plasma or serum from whole blood. Specifically, the devices of the invention comprise a matrix of hydrophilic sintered porous material in which at least one red blood cell agglutinating agent has been incorporated. The matrix is further characterized by a pore size selected such that individual blood cells will pass through the matrix but wherein agglutinated blood cells will be retained by the matrix. The devices are capable of carrying out a rapid separation of serum or plasma from whole blood while retaining only minimal quantities of serum or plasma within the interstices of the matrix.

According to one aspect of the invention, the device comprises a matrix of hydrophilic sintered porous material in which at least one red blood cell agglutinating agent has been incorporated. A sample of whole blood is applied to an inlet of the matrix and the blood cells within the sample come in contact with the agglutinating agents present in the matrix. The blood cells agglutinate and are entrapped in the interstices near the inlet of the matrix, while substantially blood-cell-free serum or plasma accumulates near an outlet of the matrix. A receiving means, including materials such as filter paper or additional porous matrices, may be incorporated in liquid receiving relationship with the outlet of the matrix. The receiving means functions to wick the substantially blood-cell-free serum or plasma from the outlet of the matrix, thus making the serum or plasma available for analysis or other purposes.

According to an alternative aspect of the invention, a filter means is incorporated in liquid receiving relationship with the outlet of the matrix for improved efficiency and more rapid separation of the blood cells from a sample of whole blood. The filter means may have at least one red blood cell agglutinating agent incorporated therein in order to assist in retaining the blood cells. The invention also provides methods and devices for the analysis of selected components of blood plasma or serum comprising the first porous matrix of the invention in combination with additional matrices or filter means in which analytical reagents selected for reaction with the selected components may be incorporated.

As indicated previously, removal of red blood cells is of particular interest in visually read assays. Nevertheless, removal of other blood cells is desirable as well, and is to be understood when the "red blood cell" is employed herein in the context of retention in the matrix or removal of whole blood.

DESCRIPTION OF THE INVENTION

The present invention provides improved devices and methods for using those devices to separate plasma or serum from whole blood. The devices of the invention comprise matrices of hydrophilic sintered porous materials in which at least one red blood cell agglutinating agent has been incorporated. The matrix is characterized by a pore size such that individual blood cells will pass through it, but wherein agglutinated cells will be retained by the matrix. The devices are capable of performing rapid separations of serum or plasma from whole blood while retaining only minimal residual quantities of serum or plasma within the interstices of the porous material.

Among the materials contemplated as being suitable for the matrices of the present invention are sintered glass, sintered steel, sintered ceramics, and sintered polymers of plastic, with the preferred material being that known as sintered polyethylene such as that described in British patent No. 2,186,205. Sintered polyethylene matrices commercially available from Porex, Inc., Fairburn, Ga. or General Polymeric Corp., West Reading, Pa. may be obtained which have a pore size of from about 10 microns to about 70 microns. Such a pore size allows individual red blood cells to pass through the matrix, but retains agglutinated red blood cells within the matrix.

The matrices of the present invention are hydrophilic so as to promote the flow of aqueous liquids through them. Commercially available matrices may be either hydrophilic or hydrophobic in nature. Hydrophobic matrices may be rendered hydrophilic by a variety of known methods. Among those methods available are plasma treatment or surfactant treatment of the matrix. Plasma treatment involves exposing the hydrophobic matrix to charged gas (plasma) wherein an electronic charge is imparted to the solid surface rendering the surface wettable. Surfactant treatment involves dipping the hydrophobic matrix in a surfactant and letting it dry. This treatment assists in wetting the surface and interior of the matrix and results in the promotion of aqueous liquid flow through the matrix. It is contemplated that a wide variety of commercially available surfactant materials would be appropriate for use with the present invention. In the assays discussed in the Examples below, commercially available matrices which had been comolded with surfactant were used and are preferred over matrices dipped in commercially available surfactants.

In general, surfactants should be selected which are compatible with the reactants or reagents placed within the matrix so as not to interfere with the preferred activity. Additionally, it should be noted that no surfactant should be present in such concentrations as to cause hemolysis of the red blood cells. In addition, care must be exercised to avoid hemodilution of the plasma sample. Hemodilution is the extraction into the plasma of the internal fluid of the red blood cell due to hypertonic conditions.

The incorporation of anti-coagulants into whole blood samples is particularly preferred for promoting the flow of plasma through the devices. Anti-coagulants mixed with the blood before application to the device prevent the blood from clotting. Separation of blood cells from a blood sample treated with anti-coagulants produces plasma. Separation of blood cells from a clotted blood sample produces serum. It is further contemplated that these anti-coagulants may be incorporated into the matrices to prevent the blood sample from clotting when applied to the device. For example, a drop of blood from a finger stick may be directly applied to the device such that anti-coagulants incorporated within the device come in contact with the blood and prevent the blood from clotting. Alternatively, blood can be collected in a capillary tube previously treated with anticoagulant, and transferred to the device in this manner. Preferred anti-coagulant materials include heparin, EDTA and citrate.

According to the invention, red blood cell agglutinating agents are incorporated into the porous matrices. Agglutinating agents are substances which cause individual red blood cells to adhere to one another to form clumps. It is contemplated that the agglutinating agents may be incorporated into a matrix by means such as adsorption, absorption or metallic-organic dye complexes, although it is preferred that at least some of the agglutinating agent be absorbed into the matrix such that it may be solubilized in the presence of a blood sample.

Suitable agglutinating agents include natural and synthetic water soluble polymers including, but not limited to, those discussed in the background. Among the available agglutinins, preferred agglutinins include hexadimethrine bromide, which is available from Aldrich Fine Chemicals as Polybrene ®, polylysine, and anti-red blood cell antibodies. It is believed that positively charged polyelectrolytes, such as Polybrene® and polylysine, aggregate erythrocytes due to charge neutralization, changes in hydration, polymer bridging and osmotic interaction. IgG- or IgM-class antibodies specific for red blood cell antigens cause agglutination by binding to similar antigenic determinants on the surface of two separate erythrocytes which causes the cells to adhere to one another. An additional enhancement of the agglutination process is achieved by incorporating substances such as polyvinyl pyrrolidone (PVP) which apparently function as dielectrics, allowing charged cells to approach one another and be cross-linked by antibody and/or other agglutinins.

A high agglutinating agent concentration results in a longer residence time for a blood sample within the matrix and increases the efficiency of agglutination of red blood cells within the matrix. This can have the undesirable effect, however, of trapping a large proportion of the plasma within the matrix. Conversely, lowering the agglutinating agent concentration allows more plasma to be released, but may result in fewer red blood cells within the sample being trapped by the matrix. The length, volume, and porosity of the matrix, as well as the volume of the blood sample to be filtered by the matrix, in addition to the agglutinating agent concentration affect the efficiency of entrapment of red blood cells within the matrix and the amount of plasma eluted by the matrix.

According to a first preferred embodiment of the device of the present invention, the pore size of the matrix is selected in conjunction with the length and volume of the matrix, the volume of blood sample to be treated, and the agglutinating agent's ability to cause the red blood cells to clump together, such that substantially all of the red blood cells present in a whole blood sample become agglutinated and are retained in the matrix. Removal of "substantially all" red blood cells present in a blood sample constitutes the removal of a sufficient amount of the red blood cells from the sample so that a clinical determination of a selected blood analyte may be performed without interference. Preferably, removal of "substantially all" red blood cells present in a blood sample constitutes the removal of at least about 90% of the red blood cells from the sample.

According to one method of utilizing the first preferred embodiment of the device of the present invention, a sample of whole blood is applied to an inlet or first end of the matrix. The blood rapidly passes through the interstices of the matrix, quickly coming in contact with the red blood cell agglutinating agents incorporated therein. These agents promote agglutination of the red blood cells which are then entrapped within the interstices of the matrix. This entrapment of the agglutinated red blood cells within the matrix permits the rapid and efficient separation of plasma or serum from the red blood cells. Additionally, because the matrix retains only a minimal amount of plasma or serum, a large amount of the plasma or serum may be successfully harvested from the whole blood sample. Optionally, a filter means such as filter paper or an additional porous matrix may be placed in liquid receiving relationship with the outlet of the matrix in order to wick the serum or plasma from the matrix.

Figure 1:
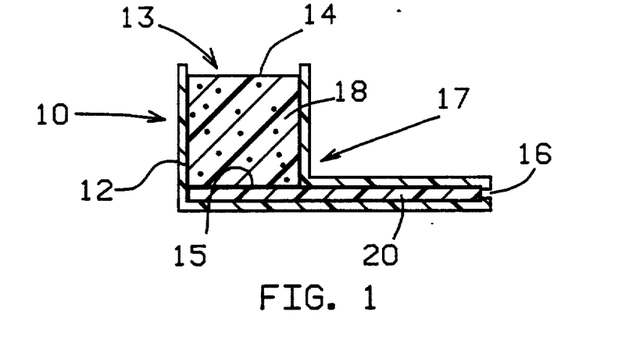
FIG. 1 is a depiction of a device comprising a porous matrix and a filter paper receiving matrix.
Figure 2:
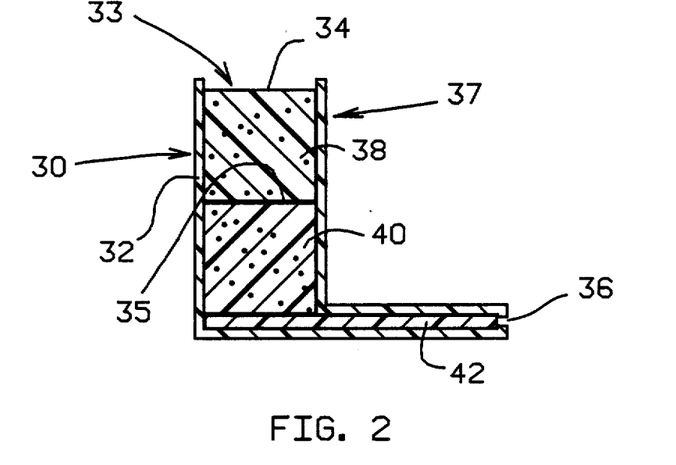
FIG. 2 is a depiction of a device comprising a first porous matrix, a second porous matrix, and a filter paper receiving matrix.

FIGS. 1-2 are depictions of exemplary devices used to separate plasma from whole blood according to the first embodiment of the present invention. As illustrated in FIG. 1, an apparatus (10) comprises a housing (12) which has an entry port (13) and an exit vent (16). Located within the housing (12) is a device (17) comprising a porous polyethylene matrix (18) which contains an agglutinating agent and is molded into a cylindrical shape having the dimensions of 3.5 mm in diameter and 5 mm in height. The exact shape and dimensions are not critical to the invention but affect resident time and efficiency as described herein. Also located within the housing (12) is a paper matrix (20). The matrix (18) has an inlet (14) and an outlet (15) and is in liquid receiving contact with said paper matrix (20). The paper matrix (20) and the matrix (18) may contain the reagents necessary for the analysis of a selected blood analyte. An embodiment of this device is described in co-owned and co-pending U.S. patent application Ser. No. 335,006, entitled Method of Ultrasonically Cutting Fibrous Materials and Device Therefrom, filed concurrently herewith and incorporated herein by reference.

As illustrated in FIG. 2, an apparatus (30) comprises a housing (32) which has an entry port (33) and an exit vent (36). Located within the housing (32) is a device (37) comprising a first porous polyethylene matrix (38). Also located within the housing (32) is a second porous polyethylene matrix (40) in liquid receiving relationship with said first matrix and a paper matrix (42) in liquid receiving relationship with said second matrix. The first matrix (38) contains an agglutinating agent and has an inlet (34) and an outlet (35). The second matrix (40) contains some of the reagents necessary for the determination of a specific blood analyte while the paper matrix (42) contains the other components of the reagent system. It is contemplated that the first matrix (38) may also contain reagents necessary for the analysis of a selected blood analyte. An exemplary dye paper reagent system is described in U.S. Ser. No. 204,443 filed June 9, 1988 and incorporated herein by reference.

According to a second preferred embodiment of the device capable of more rapid separation of red blood cells, the pore size of the matrix is selected in conjunction with the length and volume of the matrix, the volume of blood sample to be treated, and the agglutinating agent's ability to cause the red blood cells to clump together, such that less than all the red blood cells present in a whole blood sample become agglutinated and are retained in the matrix. In these cases where it is desirable to select a matrix having a relatively large pore size which provides a high rate of flow, but wherein not all the red blood cells are retained by the matrix, the red blood cells remaining in the plasma or serum are subjected to subsequent filtration steps utilizing secondary matrices or filters alone, or impregnated with red blood cell agglutinating agents, such that "clear" plasma or serum is produced. The removal of at least 97% of the red blood cells from the sample constitutes "clear" plasma or serum.

Filter paper characterized by a pore size such that agglutinated red blood cells will not pass through it may be used to purify further the serum or plasma. Additionally, this filter paper has agglutinating agents incorporated within it to aid in the retention of the remaining red blood cells. The use of filter paper as a separate barrier for the retention of the red blood cells from the serum or plasma which flows from a matrix allows for a variety of filtration formats where a series of matrices treated with agglutinating agents are interspersed with pieces of filter material. Among the types of filters contemplated for such use are filters comprised of derivatized or underivatized cellulose, nylon, natural or synthetic membranes, or porous polyethylene matrices characterized by a pore size such that individual or agglutinated red blood cells will be retained by the porous matrix. Where more than one matrix is used, pore diameters are chosen to promote flow from one region to another.

Figure 3:
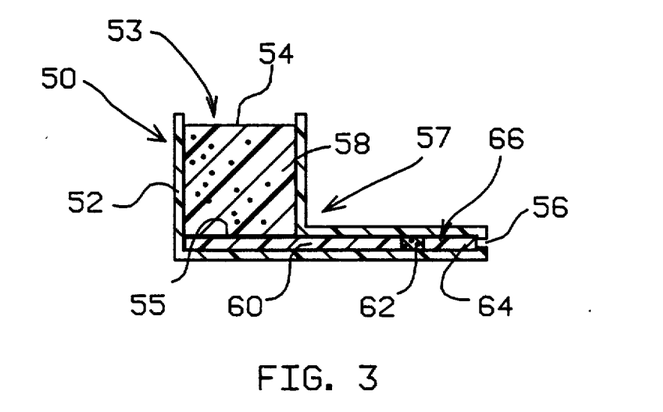
FIG. 3 is a depiction of a device comprising a porous matrix, and a filter paper receiving matrix with a reagent containing zone.
Figure 4:
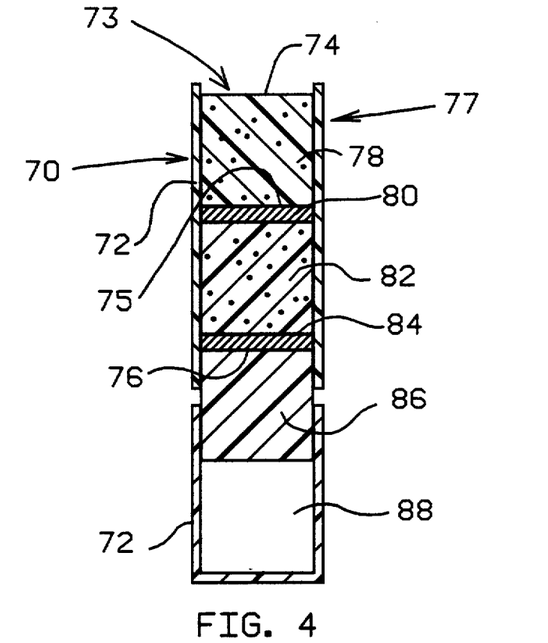
FIG. 4 is a depiction of a device comprising a first porous matrix, a first filter means, a second porous matrix, a second filter means, and a receiving porous matrix.
Figure 5:
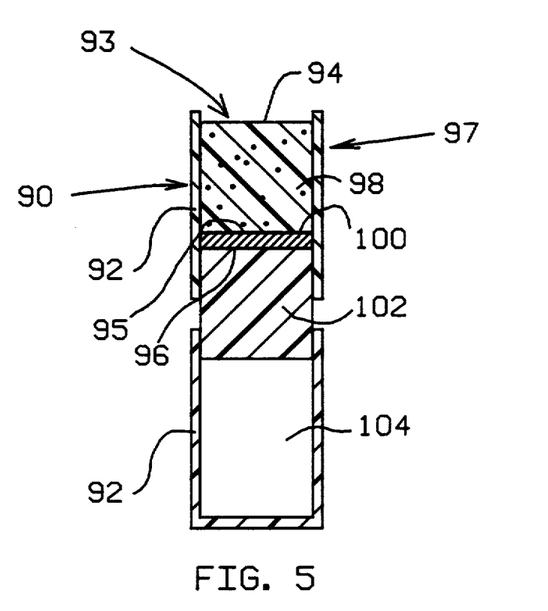
FIG. 5 is a depiction of a device comprising a porous matrix, a filter means, and a receiving porous matrix.

FIGS. 3–5 are depictions of exemplary devices used to separate plasma from whole blood according to the second embodiment of the present invention. As illustrated in FIG. 3, an apparatus (50) comprises a housing (52) which has an entry port (53) and an exit vent (56). Located within the housing (52) is a device (57) comprising a porous polyethylene matrix (58) and a paper matrix (66). The matrix (58) contains an agglutinating agent, has an inlet (54) and an outlet (55), and is in liquid receiving relationship with the paper matrix (66). The paper matrix contains a final red blood cell filtration region (60), an analyte reagent region (62), and a quantitative analysis region (64).

As illustrated in FIG. 4, an apparatus (70) comprises a housing (72) which has an entry port (73) and an exit port (76). Located within the housing (72) is a device (77) comprising a first porous polyethylene matrix (78), a first filter means (80), a second porous polyethylene matrix (82), and a second filter means (84). The first matrix (78) contains an agglutinating agent and has an inlet (74) and an outlet (75). Because the first filter means (80) is sandwiched between the first matrix (78) and the second matrix (82), the top of the first filter means (80) is in liquid receiving relationship with the outlet (75) of the first matrix (78), and the bottom of the first filter means (80) is in liquid receiving relationship with the top of the second matrix (82). The bottom of the second porous polyethylene matrix (82) is then in liquid receiving relationship with the top of the second filter means (84). Prior to addition of a blood sample to the device, it is placed on top of and in liquid receiving relationship with a third porous polyethylene matrix (86). This third matrix (86) is designed to retain and receive within its void space a selected predetermined volume of plasma which is then washed into a receiving cuvette (88). The third matrix (86) may contain some of the reagents necessary for the determination of a specific blood analyte while the cuvette (88) may contain other components of the reagent system.

As illustrated in FIG. 5, the device (90) comprises a housing (92) which has an entry port (93) and an exit port (96). Located within the housing (92) is a device (97) comprising a porous polyethylene matrix (98) and a filter means (100). The matrix (98) contains an agglutinating agent and has an inlet (94) and an outlet (95). The top of the filter means (100) is in liquid receiving relationship with the outlet (95) of the matrix (98). Prior to addition of a blood sample to the device (90), it is placed on top of and in liquid receiving relationship with a second porous polyethylene matrix (102). This second matrix (102) is designed to receive and retain a selected predetermined volume of plasma which is then washed into a receiving cuvette (104). The second matrix (102) may contain some of the reagents necessary for the determination of a specific blood analyte while the cuvette (104) may contain other components of the reagent system.

The plasma or serum which flows from the devices of the present invention may flow directly into a receiving matrix. Among the different types of matrices available which may receive the plasma or serum from the device are a dye paper matrix (see, e.g. U.S. Ser. No. 204,443 above) to which the analytical reagents have been attached or porous matrices made from sintered materials, such as glass, steel, ceramics, or plastic polymers, which are capable of retaining a selected volume of plasma or serum. According to use of the dye paper matrix, the plasma or serum enters the paper and flows as a front through the paper. It comes in contact with the analytical reagents incorporated in the paper and the assay for the desired blood component is performed on the paper.

The preferred sintered matrix capable of receiving the flow of plasma or serum from the device is a treated porous polyethylene matrix. The plasma or serum flows from the device and a selected amount enters the receiving matrix. The void space of the receiving matrix determines the volume of plasma or serum which may enter the receiving matrix. The plasma or serum is eluted from the receiving matrix into a cuvette by addition of an elution buffer. Analysis of the desired blood component occurs within the cuvette which may contain the desired analytical reagents. The porous polyethylene matrix may also contain reagents necessary for the analysis of the analyte after plasma or serum have been eluted. Such an analysis may take place in the polyethylene matrix or the sample and reagents may be eluted into the cuvette for subsequent reading.

Although the devices of the present invention may be used generally as a means for providing plasma or serum for use in other diagnostic procedures, various analytical reagents may be incorporated into the devices in order to render them suitable for carrying out an analysis for a selected component of blood plasma or serum. Among those contemplated are the reagents such as those utilized for carrying out enzymatic analysis of analytes such as cholesterol, triglycerides, and glucose in the blood. It is contemplated that reagents for a wide variety of assays may be incorporated into the devices of the present invention.

The porous matrices of the invention will retain serum or plasma in their interstices in proportion to the volume of the porous matrix. Red blood cell free plasma or serum will generally remain in the interstices of the porous matrix unless it is removed by external means. Such external means can include the use of positive hydrostatic pressure such as may be obtained by application of additional blood sample or elution buffer to the matrix. Alternatively, filter means such as filter paper or additional porous matrices in liquid receiving relationship with the matrix may be used to induce the flow of plasma or serum by capillary action out of the matrix. Accordingly, it is desired to use the smallest matrix consistent with flow and purity considerations in order to maximize serum or plasma yield.

The rate of flow of plasma and serum through the porous matrix may be controlled by varying the porosity and flow properties of the contacting filter means. It is contemplated that filter means may be selected to induce rapid flow through the porous matrix. Alternatively, where it is desired to maintain a longer residence time of blood sample within the porous matrix, a filter means providing a relatively slower rate of fluid flow out of the porous matrix may be selected. It is contemplated that slowing the rate of flow through the porous matrix can increase the efficiency of agglutination within the matrix. It is further contemplated that use of a filter means inducing a relatively slow rate of fluid flow can provide the advantage of greater agglutination efficiency and may also allow use of a smaller porous matrix thus providing the additional advantage of maximizing plasma or serum yield.

The following specific examples are directed to several embodiments of the present invention and are not to be construed as limiting the scope of the invention.

EXAMPLE 1

The device depicted in FIG. 2 contains a first matrix which has dimensions of 5 mm×4 mm×3 mm, is treated with a wetting agent and has adsorbed to it a 30 microliter solution of 5 mg/ml anti-red blood cell antibodies in 100 mM citrate, pH 5.6. The pore size of the first matrix and the agglutinating agents adsorbed to it are selected to retain substantially all red blood cells within the matrix. Loading is accomplished by saturating the first matrix with the antibody solution. Once the matrix is loaded, it is frozen and lyophilized. The second matrix, which has dimensions of 6 mm×4 mm×0.8 mm, is treated with a wetting agent and contains the reagents necessary for determination of an analyte in the plasma. Whole blood is added through the entry port and, as it percolates through the first matrix, red blood cells within the sample are agglutinated by the anti-red blood cell antibodies and the clumps are filtered out. The plasma, now free of red blood cells, flows from the first matrix into the second matrix and solubilizes the enzymes and dye component of the reagent system located there. This mixture then flows into the dye paper matrix, where determination of the analyte occurs by reaction of the blood analyte with other enzymes and dye components of the reagent system.

EXAMPLE 2

The device depicted in FIG. 3, which has dimensions of 6 mm×4 mm×0.8 mm, is treated with a wetting agent and has adsorbed to it 8 microliters of a 5 mg/ml solution of anti-red blood cell antibodies: IgG fraction (Organon Teknika Corp., Cappel Division), in 100 mM citrate buffer, pH 5.6. Loading is accomplished by applying the antibody solution to the matrix under vacuum. Once the matrix is loaded, it is frozen and lyophilized. Whole blood is added through the entry port and, as it percolates through the matrix, red blood cells within the sample are agglutinated by the anti-red blood cell antibodies and the red blood cells are partially filtered out. Final red blood cell filtration occurs in the filtration region of the dye paper matrix. As the plasma continues flowing up the dye paper matrix, it contacts the analyte reagent region where the reagents for analyte determination have been lyophilized. The plasma solubilizes these reagents and quantitation of the analyte by reaction of the sample and reagents occurs in the quantitative analysis region.

EXAMPLE 3

In this example, the device disclosed in Example 2 was used to separate plasma from whole blood so that a blood cholesterol assay could be performed. The matrix was loaded with a solution of 8 microliters of 5 mg/ml anti-red blood cell antibodies: (IgG fraction (Organon Teknika Corp., Cappel Division)), 10 mg/ml cholesterol esterase, 10 mg/ml horseradish peroxidase, and 5 mg/ml 4-aminoantipyrine in 100 mM citrate, at pH 5.6. The device was placed on top of and in contact with a dye paper matrix and whole blood was added to the device through the entry port. As the blood percolated through the porous matrix, red blood cells within it were agglutinated by the anti-red blood cell antibodies and the red blood cells were partially filtered out by the matrix. Final red blood cell filtration occurred in the region of the dye paper matrix which was 5-6 mm from the paper origin where the device contacted the dye paper matrix. At this point 5-6 mm from the paper origin, the plasma contacted an analyte determinator region which was a 3 mm wide zone that contained a solution of 100 mg/ml cholesterol oxidase, 1% (w/v) triton X-100, and 100mM NaPO$_4$, at pH 6.8. As the plasma flowed up the paper matrix it solubilized the lyophilized reagents. The flow continued into the dye paper matrix where quantitation of the analyte (cholesterol) occurred.

EXAMPLE 4

With respect to the device depicted in FIG. 1, the matrix was treated with a wetting agent and had adsorbed to it various 25 microliter solutions of anti-red blood cell antibodies: IgG fraction (Organon Teknika Corporation, Cappel Division), in 20 mM citrate buffer, pH 5.6. In this device, the data listed in Table 1 below indicated that a 2 mg/ml antibody concentration loaded under vacuum was optimal for filtering out red blood cells from whole blood having a hematocrit of 30–60% red blood cells and releasing at least 5 microliters of plasma from a 25 microliter sample of whole blood. Hematocrit refers to the percentage of the volume of a blood sample occupied by red blood cells. For example, a 25 microliter blood sample with a hematocrit of 30 contains 7.5 microliters of red blood cells and 17.5 microliters of plasma. The whole blood samples were treated with heparin as an anticoagulant. This concentration of antibody allowed plasma to flow 12 mm to the end of the filter paper in a reasonable amount of time, while still retaining substantially all the red blood cells of a sample within the matrix. Higher antibody concentrations resulted in greater agglutination which blocked the pores within the matrix and precluded flow of plasma. The pore size of the matrix and the agglutinating agents adsorbed to it were selected to retain substantially all red blood cells within the matrix. Loading was accomplished by applying the antibody solution to the matrix by saturation, i.e. soaking the matrix in solution, or under vacuum, i.e. soaking the matrix in solution and pulling a vacuum on it for 10 minutes. It was determined that loading under vacuum was superior to loading by saturation because vacuum loading ensures that no air pockets remain in the matrix after loading. Loading by saturation does not ensure this same result. Once the matrix was loaded, it was frozen and lyophilized. The trials were run in sets of 6 and a trial was determined to be "substantially free" of red blood cells (i.e. "No RBCs") by the visual determination that there were no red blood cells in the filter paper, which was in liquid receiving relationship with the matrix, after the filtration step. In the table, "seconds to end" refers to the elapsed time from the addition of a blood sample to the inlet of the matrix, until plasma reached the end of the filter means.

TABLE 1

| | ANTI-RED BLOOD CELL ANTIBODIES (mg/ml) | | | | |
|---|---|---|---|---|---|
| | 1 | 2 | 3 | 4 | 5 |
| HEMATOCRIT = 30 | | | | | |
| Saturated | | | | | |
| seconds to end | 74.5 | 82.0 | 104.2 | 159.7 | 219.3 |
| no RBCs | 2/6 | 5/6 | 6/6 | 6/6 | 5/5 |

TABLE 1-continued

|  | ANTI-RED BLOOD CELL ANTIBODIES (mg/ml) | | | | |
| --- | --- | --- | --- | --- | --- |
|  | 1 | 2 | 3 | 4 | 5 |
| Vacuum |  |  |  |  |  |
| seconds to end | 65.3 | 70.2 | 105.2 | 84.2 | 108.8 |
| no RBCs | 2/6 | 4/6 | 6/6 | 6/6 | 6/6 |
| HEMATOCRIT = 45 |  |  |  |  |  |
| Saturated |  |  |  |  |  |
| seconds to end | 200.0 | 290.0 | 585.6 | 631.7 | 469.8 |
| no RBCs | 5/6 | 6/6 | 5/5 | 5/5 | 5/5 |
| HEMATOCRIT = 45 |  |  |  |  |  |
| Vacuum |  |  |  |  |  |
| seconds to end | 107.0 | 326.7 | 193.0 | 414.8 | n.f. |
| no RBCs | 6/6 | 4/4 | 5/5 | 6/6 | n.f. |
| HEMATOCRIT = 60 |  |  |  |  |  |
| Saturated |  |  |  |  |  |
| seconds to end | 336.7 | 700.7 | n.f. | n.f. | n.f. |
| no RBCs | 2/3 | 3/3 | n.f. | n.f. | n.f. |
| Vacuum |  |  |  |  |  |
| seconds to end | 354.3 | 824.5 | n.f. | n.f. | n.f. |
| no RBCs | 5/5 | 4/4 | n.f. | n.f. | n.f. | n.f. = no flow of plasma to end of filter paper matrix.

At a low blood hematocrit (e.g. 30), up to 15 microliters of plasma may be released from a 25 microliter sample of whole blood in as little as 2 minutes, while at a high blood hematocrit (e.g. 60), about 5 microliters of plasma may be released from a 25 microliter sample of whole blood in around 15 minutes.

EXAMPLE 5

In this example, the device disclosed in Example 3 was used to separate plasma from whole blood so that an assay to detect antibodies to Human Immunodeficiency Virus (HIV) could be performed. The matrix was loaded with 8 microliters of 5 mg/ml anti-red blood cell antibodies: (IgG fraction (Organon Teknika Corp. Cappel Division)), 5 microliters detector label prepared by binding 10 micrograms/ml HIV antigen with 0.05% black latex as described in co-owned and copending U.S. patent application Ser. No. 248,858 filed Sept. 23, 1988, poly(pyrrole), in aqueous suspension at pH 7.0. The device was placed on top of and in contact with a 3×30 mm strip of nitrocellulose (S & S, Keene, NH), which had a 5 micrometer pore size, and 30 microliters of whole blood were added to the device through the entry port. As the blood percolated through the porous matrix, red blood cells within it were agglutinated by the anti-red blood cell antibodies and the red blood cells were partially filtered out by the matrix. The plasma in the sample mixed with the label suspension in the matrix and then entered the nitrocellulose strip where final red blood cell filtration and analysis of the separated plasma occurred.

EXAMPLE 6

To the device depicted in FIG. 4, whole blood is added through the entry port. As the blood percolates through the first matrix, red blood cells within the sample are agglutinated by the anti-red blood cell antibodies and the red blood cells are partially filtered out. The remaining red blood cells and smaller clumps of agglutinated red blood cells pass into the first filter where additional separation of plasma from the red blood cells occurs. Those red blood cells not retained by the first filter pass into the second matrix where additional separation of plasma from the red blood cells occurs. Finally, any red blood cells not retained by the second matrix pass into the second filter, to which at least one red blood cell agglutinating agent has been adsorbed, where agglutination of the remaining red blood cells in the plasma occurs. The plasma then flows into the receiving matrix where the plasma volume is quantitated. The red blood cell filtration stack is separated from the receiving matrix and the selected volume of plasma is eluted into an attached cuvette by the addition of the elution buffer. The cuvette may contain various analytical reagents. Thorough mixing of the plasma and the elution buffer is accomplished by inverting the cuvette 2 times. After a specified waiting period, the results of the test are obtained by comparing the color of the liquid with a standard chart.

Specifically, with respect to the device depicted in FIG. 4, the pore size of the first matrix (Porex 4897) and the agglutinating agents adsorbed to it were selected to agglutinate and retain most, but not all, red blood cells within the first matrix. The first matrix is molded into a cylindrical shape having the dimensions of 0.2 inches in diameter and 0.07 inches in length and had adsorbed to it 15.0 microliters of a solution of 0.44% (w/v) antiserum to red blood cells (Organon Teknika Corp., Cappel Division), 4.4% (w/v) Polybrene (Aldrich Fine Chemicals), and 4.4% (w/v) PVP (Aldrich Fine Chemicals) in 0.35 mM citrate buffer, pH 7.4 (Fisher Chemicals). The coated first matrix was dried in a hot air oven. The composition of the solution and the quantity loaded into the first matrix were chosen to provide very rapid red blood cell agglutination without causing red blood cells to lyse and without causing hemodilution. The remaining red blood cells were removed from the plasma by passing it through the first filter means (Whatman 31 ET), the second porous polyethylene matrix (Porex 4932), and the second filter means (Whatman 31 ET). This last filter means had incorporated within it 36.1 microliters/cm$^2$ of a 1 mg/ml solution of antiserum to red blood cells. The coated last filter means was dried in a hot air oven. This device produced 15 microliters of clear plasma 99% free of hemoglobin from 50 microliters of blood within 3 minutes as shown in Table 2. Upon removal of the red blood cell filtration stack, i.e. the first matrix, the first filter means, the second matrix, and the second filter means, the plasma was eluted into a cuvette by the addition of an elution buffer.

EXAMPLE 7

To the device depicted in FIG. 5, whole blood is added through the entry port. As the blood percolates through the matrix, red blood cells within the sample are agglutinated by the anti-red blood cell antibodies and the red blood cells are partially filtered out. The remaining red blood cells and smaller clumps of agglutinated red blood cells pass into the filter where additional separation of plasma from the red blood cells occurs. The plasma then flows into the receiving matrix where the plasma volume is quantitated. The red blood cell filtration stack is separated from the receiving matrix and the selected volume of plasma is eluted into an attached cuvette by the addition of the elution buffer. The cuvette may contain various analytical reagents. Thorough mixing of the plasma and the elution buffer is accomplished by inverting the cuvette 2 times. After a specified waiting period, the results of the test are obtained by comparing the color of the liquid with a standard chart.

Specifically, with respect to the device depicted in FIG. 5, the pore size of the matrix (Porex 4897) and the agglutinating agents adsorbed to it were selected to agglutinate and retain most, but not all, red blood cells within the matrix. The matrix had adsorbed to it 15.0 microliters of a solution of 0.88% (w/v) antiserum to red blood cells (Organon Teknika Corp., Cappel Division), 1.76% (w/v) Polybrene (Aldrich Fine Chemicals), and 1.76% (w/v) PVP (Aldrich Fine Chemicals) in 0.397 mM citrate buffer, pH 7.4 (Fisher Chemicals). The coated matrix was dried in a hot air oven. The composition of the solution and the quantity loaded into the matrix were chosen to provide very rapid red blood cell agglutination without causing red blood cells to lyse and without causing hemodilution. The remaining red blood cells were removed from the plasma by passing it through the filter means (Whatman 1CHR). The filter means had incorporated within it 15.0 microliters/cm$^2$ of a 1 mg/ml solution of antiserum to red blood cells. The coated filter means was dried in a hot air oven. This device produced 10 microliters of clear plasma 99% free of hemoglobin from 40 microliters of blood within 2 minutes as shown in Table 3. Upon removal of the red blood cell filtration stack, i.e. the matrix and the filter means, the plasma was eluted into a cuvette by the addition of an elution buffer.

Numerous modifications and variations are expected to occur to those skilled in the art upon consideration of the foregoing descriptions of preferred embodiments thereof. Consequently, only such limitations should be placed upon the scope of the invention as appear in the appended claims.

consisting of sintered glass, sintered steel, sintered ceramics, and sintered plastics.

3. The device according to claim 1, wherein said sintered porous material is polyethylene.

4. The device according to claim 1, wherein the pore size of said matrix is from about 10 microns to about 70 microns, and the quantity and type of agglutinating agents are selected such that at least 95% of the red blood cells contained within a blood sample added to the device are retained by the matrix.

5. The device according to claim 1, further comprising a filter means in liquid receiving relationship with said matrix.

6. The device according to claim 5 wherein said filter means is capable of retaining blood cells which pass through said matrix.

7. The device according to claim 6, wherein at least one red blood cell agglutinating agent has been incorporated into said filter means.

8. The device according to claim 5, wherein said filter means is selected from the group consisting of derivatized or underivatized cellulose filter and porous polyethylene matrices.

9. The device according to claim 5, wherein the pore size of said matrix is from about 10 microns to about 70 microns, and the quantity and type of agglutinating agents are selected such that at least 97% of the red blood cells contained within a blood sample added to the device are retained by said matrix and filter.

10. The device according to claim 1, further compris-

TABLE 2

BLOOD SEPARATOR PERFORMANCE OF FOUR LAYER STACK
(POREX -31ET-POREX-31ET. POREX)

| Receiving Frit Dimension | | Blood Sample Volume (uL) | Hematocrit of Sample (%) | Time | | | Plasma Volume Quantitate (uL) |
|---|---|---|---|---|---|---|---|
| Diameter (mm) | Thickness (mm) | | | Plasma Appeared in Frit (Seconds) | Frit Appeared Full (Seconds) | Device Separated (Seconds) | |
| 3.5 | 3.4 | 50 | 25 | 10 | 60 | 120 | 15.5 |
| | | 50 | 38 | 15 | 90 | 120 | 15.3 |
| | | 50 | 50 | 20 | 120 | 180 | 15.1 |
| | | 50 | 75 | 60 | NO | 900 | about 5 |
| | | 75 | 75 | 50 | NO | 600 | about 10 |

TABLE 3

BLOOD SEPARATOR PERFORMANCE OF TWO LAYER STACK
(POREX-1chr.POREX)

| Receiving Frit Dimension | | Blood Sample Volume (uL) | Hematocrit of Sample (%) | Time | | | Plasma Volume Quantitate (uL) |
|---|---|---|---|---|---|---|---|
| Diameter (mm) | Thickness (mm) | | | Plasma Appeared in Frit (Seconds) | Frit Appeared Full (Seconds) | Device Separated (Seconds) | |
| 3.5 | 1.7 | 35 | 35 | 10 | 30 | 120 | 8.7 |
| | | 35 | 40 | 10 | 30 | 120 | 8.6 |
| | | 35 | 45 | 10 | 40 | 120 | 8.5 |
| | | 35 | 50 | 15 | 40 | 120 | 8.4 |
| | | 40 | 55 | 15 | 50 | 120 | 8.3 |
| | | 50 | 60 | 20 | 60 | 120 | 8.2 |

We claim:

1. A device for separating plasma or serum from whole blood comprising a matrix of hydrophilic sintered porous material in which at least one red blood cell agglutinating agent has been incorporated, said matrix being characterized by a pore size selected such that individual blood cells pass through said matrix but agglutinated blood cells are retained by said matrix.

2. The device according to claim 1, wherein said sintered porous material is selected from the group ing a second matrix of hydrophilic sintered porous material in liquid receiving relationship with said first matrix which is capable of receiving a selected predetermined amount of plasma or serum from said first matrix.

11. The device according to claim 1, comprising said first matrix; a first filter means in liquid receiving relationship with said first matrix; a second matrix of hydrophilic porous material in liquid receiving relationship with said first filter means; a second filter means in which at least one red blood cell agglutinating agent has been incorporated in liquid receiving relationship with said second matrix; and a third matrix of hydrophilic sintered porous material in liquid receiving relationship with said second filter means which is capable of receiving a selected amount of plasma or serum.

12. The device according to claim 1, further comprising additional matrices or filter means in liquid receiving relationship with the first matrix, wherein an analytical reagent selected for reaction with a selected component is incorporated within a member selected from the group consisting of said matrices and said filter means.

13. A method for separating plasma or serum from whole blood comprising the steps:
 (a) applying a sample of whole blood to an inlet of a device comprising a matrix of hydrophilic sintered porous material in which at least one red blood cell agglutinating agent has been incorporated, said matrix being characterized by a pore size selected such that individual blood cells pass through said matrix but agglutinated blood cells are retained by said matrix; and
 (b) collecting the plasma or serum from an outlet of the device.

14. The method according to claim 13, wherein the pore size of said matrix and the quantity and type of agglutinating agents are selected such that at least of red blood cells contained within said blood sample are retained by the matrix.

15. The method according to claim 13, wherein said blood sample which has been applied to the inlet of said matrix is passed into a filter means in liquid receiving relationship with the outlet of said matrix.

16. The method according to claim 15, wherein said filter means functions to retain blood cells which pass through said matrix.

17. The method according to claim 15, wherein the pore size of said matrix and the quantity and type of agglutinating agents are selected such that at least 97% of red blood cells within said blood sample are retained by said matrix and filter.

18. The method according to claim 13, wherein said plasma or serum is collected by means of a second matrix of hydrophilic sintered material in liquid receiving relationship with said first matrix.

19. The method according to claim 18, wherein said plasma or serum is eluted from said second matrix by means of an elution buffer.

20. A method for the analysis of a selected component of blood plasma or serum utilizing a device according to claim 12, said method comprising the steps of applying a sample of whole blood to be analyzed to the first matrix and carrying out at least one chemical or immunological reactions for the analysis of said selected component.

* * * * *

UNITED STATES PATENT AND TRADEMARK OFFICE
CERTIFICATE OF CORRECTION

PATENT NO. : 4,933,092

DATED : June 12, 1990

INVENTOR(S) : D. Aunet, et al.

It is certified that error appears in the above-identified patent and that said Letters Patent is hereby corrected as shown below:

Column 15, line 29:

Claim 14, line 3, after "least" insert --95%--.

Signed and Sealed this

Twentieth Day of August, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO.   :  4,933,092
DATED        :  June 12, 1990
INVENTOR(S)  :  D. Aunet, et al.

It is certified that error appears in the above-identified patent and that said Letters Patent is hereby corrected as shown below:

Title page:   Inventor "GEROGEVICH" is misspelled;  Should be changed to "GEORGEVICH".

Signed and Sealed this

Twenty-sixth Day of November, 1991

*Attest:*

HARRY F. MANBECK, JR.

*Attesting Officer*    *Commissioner of Patents and Trademarks*